United States Patent [19]

Rounbehler et al.

[11] 4,381,408
[45] Apr. 26, 1983

[54] METHOD AND APPARATUS FOR EXTRACTION OF AIRBORNE AMINE COMPOUNDS

[75] Inventors: David P. Rounbehler, Concord; John W. Reisch, Brookline, both of Mass.

[73] Assignee: Thermo Electron Corporation, Waltham, Mass.

[21] Appl. No.: 225,285

[22] Filed: Dec. 1, 1980

Related U.S. Application Data

[63] Continuation of Ser. No. 61,552, Jul. 27, 1979, Pat. No. 4,249,904.

[51] Int. Cl.³ .................... G01N 31/06; G01N 31/08
[52] U.S. Cl. .................... 564/112; 564/437; 564/497; 564/498; 436/107; 436/111; 436/181
[58] Field of Search ............... 252/184, 193, 188.3 R, 252/426, 436, 439, 428, 438; 564/497, 498, 437, 112, 113; 423/212, 236, 239, 245 S; 55/70, 74; 23/232 R, 232 C, 230 M; 422/88, 89

[56] References Cited

U.S. PATENT DOCUMENTS

| | | | |
|---|---|---|---|
| 1,864,988 | 6/1932 | Downs | 252/428 |
| 2,237,459 | 4/1941 | Thompson | 252/436 |
| 2,547,064 | 4/1951 | Tyerman | 564/499 |
| 3,469,934 | 9/1969 | Bocard et al. | 423/245 S |
| 3,855,298 | 12/1974 | Bathellier | 564/499 |
| 3,996,002 | 12/1976 | Fine | 23/230 PC |
| 4,003,257 | 1/1977 | Fletcher et al. | 73/23.1 |
| 4,131,544 | 12/1978 | Elahi | 23/230 B |
| 4,194,884 | 3/1980 | Rounbehler et al. | 23/232 R |

OTHER PUBLICATIONS

Russell, John W., *Environmental Science and Technology*, vol. 9, No. 13, Dec. 1975, p. 1175.

Fine, D. H. et al., *Environmental Science and Technology*, vol. 11, No. 6, Jun. 1977, p. 577.

*Primary Examiner*—Michael S. Marcus
*Attorney, Agent, or Firm*—Herbert E. Messenger; James L. Neal

[57] ABSTRACT

A method and apparatus are disclosed for extracting amine compounds from air samples without loss due to formation of nitrosamine artifacts. The apparatus includes a cartridge having a separation zone between a first port and a second port. The separation zone contains an air pervious packing of a granular, solid phase amine complexing agent. The method includes a first step of driving an air sample through the separation zone of the cartridge from the first port to the second port, and a second step of driving an eluent through the separation zone from the second port to the first port, or backflushing the cartridge. To extract amine compounds, the eluent is a solvent for the amine complexing agent in the separation zone of the cartridge. The method may contain the further step of determining the amine compound concentration of at least a portion of the eluate which passes from the separation zone following the second step of the method.

3 Claims, 3 Drawing Figures

METHOD AND APPARATUS FOR EXTRACTION OF AIRBORNE AMINE COMPOUNDS

This is a continuation of application Ser. No. 61,552, filed July 27, 1979 now U.S. Pat. No. 4,249,904.

CROSS REFERENCE TO RELATED APPLICATIONS

This application is related to U.S. patent application Ser. No. 963,626, entitled "Method and Apparatus for Air Sampling and Filtration", filed Nov. 24, 1978, and issued Mar. 25, 1980, as U.S. Pat. No. 4,194,884, and to U.S. patent application Ser. No. 061,554, entitled "Method and Apparatus for Extraction Of Airborne N-Nitroso Compounds Without Artifact Formation", filed on even date herewith. Those applications are incorporated by reference herein.

BACKGROUND OF THE INVENTION

This invention relates to air sampling systems and more particularly to methods and apparatus for removing amine compounds from air samples.

Devices and methods are known for sampling air to identify types and levels of amine compounds present in the environment. These compounds may arise from a variety of sources, such as the manufacture and use of chemicals, combustion of fuels, and others. The conventional method for extraction of airborne amine compounds requires the air sample to pass over a bed of silica gel to trap the amines therein. Following this first step, the silica gel is then washed with a solution of 0.2 N sulfuric acid in 10% methanol to remove the trapped amine compounds. The resultant wash may then be gas chromatographically separated into its constituent amine compounds. This method, however, is generally ineffective for air samples which include oxides of nitrogen. More particularly oxides of nitrogen (for example NO, $N_2O_3$ and $N_2O_4$) may readily undergo a gas phase N-nitrosation reaction with the amines trapped on the silica gel. Consequently, the analysis of the amine-containing wash results in errors due to the amines which have been nitrosated. As a result "detected" amine compounds do not include the amines from the original sample which have been converted to N-nitroso compounds by N-nitrosation during the collection and analysis process. Consequently, an accurate air sampling and amine compound detection system must be effective in atmospheres in which reactive compounds are present in large concentrations.

Accordingly, it is a general object of this invention to provide improved methods and apparatus for removing amine compounds from air.

It is another particular object of the invention to provide an improved method and apparatus for determining the concentration of amine compounds in an air sample without formation of nitrosamines from amines in the sample.

It is also an object of the invention to provide apparatus for collecting amine compounds from air which is compact, inexpensive, portable, and simple to use.

SUMMARY OF THE INVENTION

The present invention is directed to methods and apparatus for extracting amine compounds from an air sample without the formation of nitrosamine artifacts from amines in the sample. According to the invention, the extraction apparatus includes a cartridge having a separation zone between two ports. The separation zone includes an air pervious packing of a granular, solid-phase amine complexing agent, such as sulfamic acid.

The cartridge may be used in conjunction with known analytical techniques, such as mass-spectroscopy, chromatography and selective pyrolysis, to provide accurate quantitative analysis of air samples.

In accordance with the method of the invention, to extract amine compounds, as a first step, an air sample may be injected at the first port of the cartridge, passed through the separation zone and out the second port. During this first step, the complexing agent in the separation zone is effective to trap substantially all amines present in the air sample within that zone, thereby inhibiting N-nitrosation. As a result, there is no nitrosamine artifact formation in the separation zone.

Following the first step, the cartridge is backflushed by an eluent which is injected at the second port, and passed through the separation zone and out the first port. The eluent is selected to be a solvent for both amines and the complexing agent in the separation zone. By way of example, where the complexing agent in the zone is sulfamic acid, a suitable eluent is acetone.

During this second step, as the eluent passes through the separation zone, the amine complexing agent in that zone is dissolved, freeing the amine compounds in the solution. Consequently, as the eluent emerges from the separation port, that eluent contains the full amount of amine compounds that had previously been trapped in the separation zone, with substantially no losses due to nitrosamine formation from some of the amines from the original air sample. This solution of the eluent and amine compounds may then be collected as it emerges from the first port, and analyzed for various amine compound content by conventional techniques.

It is an important feature of the air sampling apparatus and method of this invention that a simple, inexpensive, rapid sampling technique is provided for extraction of low level amine compound concentrations. It is an additional important feature that with the invention, substantially all the amines from the original sample may be collected and analyzed without loss due to N-nitrosation.

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENT

Figure 1:
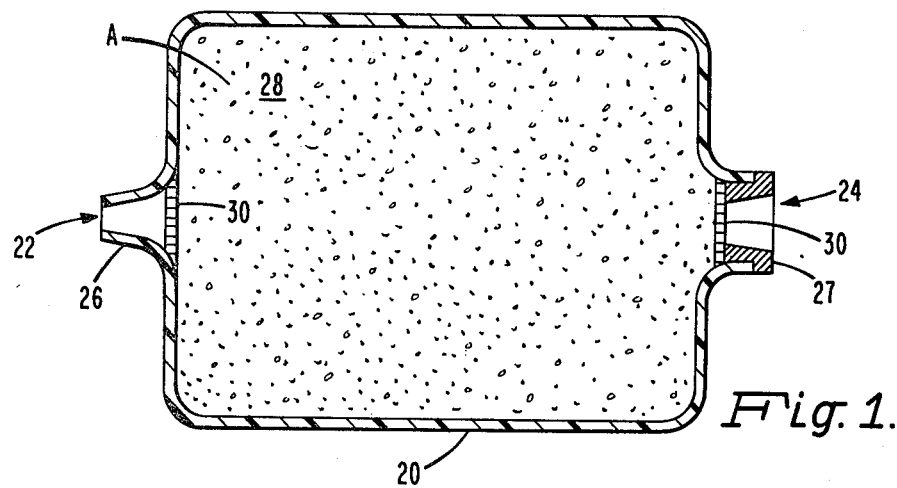
FIG. 1 shows in sectional view an amine collection device in accordance with the present invention.

FIG. 1 shows a sectional view of a cartridge 20 which may be used to separate amines from an air sample. Cartridge 20 is a thin-walled tube including a first port 22, a second port 24, and a separation zone (denoted A) between port 22 and port 24. Cartridge 20 is a polyethylene cylinder having a 15 mm inner diameter and a 20 mm depth. The port 24 includes a ring-shaped adapter 27 to permit the insertion of the tip of a syringe for injecting a liquid phase eluent into the cartridge 20 through port 24. The walls 26 of port 22 are tapered away from the separation zone A to help direct the flow of the liquid phase eluent from the cartridge 20 during collection.

In the preferred embodiment, zone A includes a packing 28 of a solid-phase, granular amine complexing agent (e.g. 30-80 mesh, granular sulfamic acid). With this configuration, the packing 28 is pervious to the flow of air therethrough.

Stainless steel screens (100 mesh) 30 are positioned at the interior of ports 22 and 24 to hold packing 28 in place.

Figure 2:
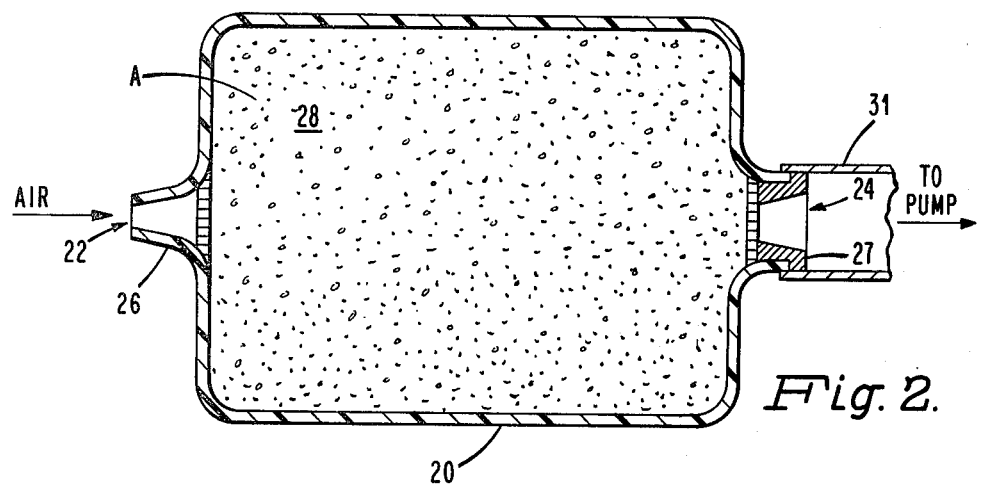
FIGS. 2 and 3 illustrate the method of the present invention, as practiced with the embodiment of FIG. 1.
Figure 3:
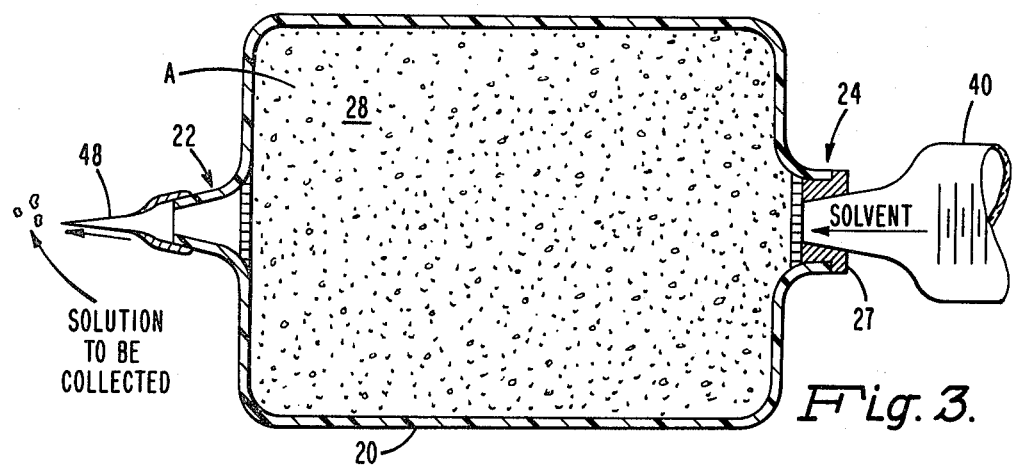

In operation, as a first step (FIG. 2), an air sample is drawn (by a pump, not shown) in succession through port 22, zone A, and port 24. As a second step (FIG. 3), the pump is disconnected, and a liquid phase eluent is injected (e.g. by means of a syringe 40) into port 24, and passed in succession through zone A and port 22. At port 22, the eluate passes through a hollow needle (which ensures that the eluent does not "channel" in cartridge 20, but rather wets all of packing 28). The eluent is a solvent for amine compounds and the amine complexing agent in zone A, or mixtures of such solvents. By way of example, acetone may be used as the eluent.

After the elution step, the eluate solution is analyzed according to known techniques to identify and quantify various amine compounds present in the eluate.

During the first step described above, the amine complexing agent in packing 28 is effective to physically trap amines from the air sample as that sample passes through zone A. The dimensions of zone A and the packing density of the granular complexing agent are selected to both accommodate a desired air flow rate and ensure that substantially all such amines are trapped. As a result of this trapping, there are substantially no amines available in zone A to undergo N-nitrosation as the input air sample passes through that zone.

During the second step, the eluent dissolves complexing agents and trapped amines. Since there was substantially no N-nitrosation during the first step, the eluate which passes through the port 22 includes substantially all of the amine compounds from the original air sample.

In the present embodiment, sulfamic acid is used as the packing for zone A. However, in alternative embodiments, other granular, solid-phase amine complexing agents might be used, such as acids (particularly ascorbic acid) or ammonium sulfamate, for example.

The solvent or eluent employed to dissolve the complexing agent 28 and the amine compounds is determined in part by the requirement that chemical reactions not occur between the eluent and the complexing agent or compounds trapped thereby, and, in addition, by the nature of the analytical techniques to be applied to measure the content of selected compounds removed from collection tube 20. In the present embodiment, the eluent is acetone. However, in alternative embodiments, ethanol, methanol, ammonia, pyridine, methyl cyanide, or pyrrolidine, or mixtures of any of these solvents or acetone may be used. Such mixtures may also be mixed with other solvents, such as dichloromethane (DCM). In still other embodiments, any polar, or nitrogenous based solvent, which is effective to dissolve both amines compounds, and the complexing agent, including water, may be utilized.

In alternative embodiments, the cartridge 20 may include additional zones between separation zone A and port 24 in accordance with the present invention. For example, the two zone cartridge disclosed in the incorporated reference Ser. No. 661,554, filed on even date herewith, may be used as an alternative embodiment of the present invention, provided that the amine complexing agent in packing 28 (zone A) is soluble in the eluent used in the backflush step. When the condition is met, the eluate contains the trapped amines from the air sample, as well as N-nitroso compounds which might also have been present in the air sample. Conventional separation techniques may be utilized to separate the amines and N-nitroso compounds.

In some forms of the invention, it may be desirable to include an additional zone within the cartridge, such as a drying zone for extracting water from an air sample. In such forms, the drying zone may be positioned between the air sample input port and the separation zone. By way of example, where the amine complexing agent is sulfamic acid, the drying zone might include an air pervious packing of sodium sulfate and calcium carbonate.

In some uses of the invention, a wash step might be utilized between the step of passing the air sample through the cartridge and the backflushing step. This wash step might comprise passing a solvent for materials other than amines and the complexing agent through the cartridge to remove organic materials which might interfere with the subsequent analysis steps. By way of example for the preferred embodiment, a wash solvent such as hexane or pentane might be used to remove benzene.

While the above disclosed embodiments of the present invention are particularly adapted for use as part of a sampling system for quantitative analysis of amine compounds in air, the essential principles of collection are applicable to air filtration and the cartridges may be readily modified for use in such devices as gas masks, hoods for chemical apparatus, and various other air-conditioning apparatus.

Accordingly, the apparatus and method of the present invention may be used to efficiently collect and determine concentrations of amines from an air sample without loss of amines due to the artifact formation of N-nitroso compounds in the sample.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. Method of extracting amine compounds and nitrosamine compounds from an air sample for quantitative analysis without loss due to formation of nitrosamine artifacts comprising the successive steps of:

A. passing said sample through a first port, a first interior zone, a second zone, and a second port of a cartridge in succession, said first interior zone containing an air pervious packing of a first granular, solid-phase amine complexing agent and said second zone containing an air pervious packing of a mixture of a second granular, solid-phase amine complexing agent and a particulate sorbent adapted to extract and concentrate nitrosamines from air; and B. passing an eluent through said second port, said second interior zone, said first interior zone, and said first port in succession, said eluent being a solvent for amine compounds, nitrosamines, and said amine complexing agents.

2. Method as in claim 1 comprising the further steps of collecting at least a portion of the eluate emerging from said first port and determining the concentration of amine compounds in said portion.

3. Method as in claim 1 wherein said first and second complexing agents are sulfamic acid, said sorbent is magnesium silicate, and said eluent is acetone.

* * * * *